(12) United States Patent
Zeng et al.

(10) Patent No.: US 9,969,995 B2
(45) Date of Patent: May 15, 2018

(54) METHODS FOR RECOMBINANT EXPRESSION OF BETA-GLUCOSIDASE GENE

(71) Applicant: Wilmar (Shanghai) Biotechnology Research & Development Center Co., Ltd., Shanghai (CN)

(72) Inventors: Ana Zeng, Shanghai (CN); Gang Wang, Shanghai (CN); Qi Feng, Shanghai (CN); Jun Xu, Shanghai (CN)

(73) Assignee: Wilmar (Shanghai) Biotechnology Research & Development Center Co., Ltd., Shanghai (CN)

( * ) Notice: Subject to any disclaimer, the term of this patent is extended or adjusted under 35 U.S.C. 154(b) by 0 days. days.

(21) Appl. No.: 15/529,657

(22) PCT Filed: Nov. 27, 2015

(86) PCT No.: PCT/CN2015/000826
§ 371 (c)(1),
(2) Date: May 25, 2017

(87) PCT Pub. No.: WO2016/082305
PCT Pub. Date: Jun. 2, 2016

(65) Prior Publication Data
US 2017/0327807 A1 Nov. 16, 2017

(30) Foreign Application Priority Data
Nov. 27, 2014 (CN) .......................... 2014 1 0699758

(51) Int. Cl.
*C12N 15/80* (2006.01)
*C12N 9/42* (2006.01)
*C12N 9/58* (2006.01)

(52) U.S. Cl.
CPC ............. *C12N 9/2445* (2013.01); *C12N 9/58* (2013.01); *C12Y 302/01021* (2013.01); *C12Y 304/23* (2013.01); *C07K 2319/00* (2013.01)

(58) Field of Classification Search
None
See application file for complete search history.

(56) References Cited

U.S. PATENT DOCUMENTS 8,546,106 B2   10/2013  Merino
8,735,549 B2   5/2014   Merino
8,871,486 B2   10/2014  Merino
9,006,409 B2   4/2015   Merinos
2011/0136197 A1   6/2011  Dodge et al.
2014/0024098 A1   1/2014  Dodge et al.

FOREIGN PATENT DOCUMENTS

CN   200980107269.7   3/2009
CN   101516906        8/2009
CN   102220369 B      10/2012
CN   101516906 B      11/2013

OTHER PUBLICATIONS de Groot, M.J. et al., "Agrobacterium tumefaciens-mediated transformation of filamentous fungi", Nature Biotechnology, vol. 16, pp. 839-842 (1998).
Penttila, M.E., et al., "Expression of two Trichoderma reesei Endoglucanase in the Yeast *Saccharomyces cereviae*", Yeast, vol. 3, pp. 175-185 (1987).
Venturi, et al., Extracellular β-D-glucosidase from *Chaetomium thermophilum* var. coprophilum: production, purification and some biochemical properties, J. Basic Microbiol., vol. 42, pp. 55-66 (2002).
Wang, Zhen-Yu, et al., "Enzyme activities of endo-cellulase and β-glucosidase produced by thermo-anaerobic Clostridium strain", Journal of Dalian Institute of Light Industry, vol. 24, No. 2, pp. 110-114 (2005).
Ma Teng, "Screening the Aspergillus niger Strain of Over-expression Thermostable beta-glucosidase and its Gene Cloning", Hebei Normal University of Science & Technology, Thesis Dissertation (2012).
Zhu, Hui-Yuan, "Expression analysis of specific genes expressed in Aspergillus niger under xylan induction and construction of a Penicillium chrysogenum strain high-expressed alkaline xylase", Shandong University, Doctoral Dissertation (2010).
Wang, Alice, et al., "Site-Specific Mutagenesis of the Human Interleukin-2 Gene: Structure-Function Analysis of the Cysteine Residues", Science, 224: 1431 (1984).

*Primary Examiner* — James S Ketter
(74) *Attorney, Agent, or Firm* — Coats & Bennett, PLLC

(57) ABSTRACT

Provided is a method for recombinant expression of β-glucosidase gene. Also provided is a recombinant expression vector comprising: (a) a coding sequence of an aspartic protease or active fragment thereof, (b) a coding sequence of β-glucosidase or active fragment thereof, and optionally (c) a linker sequence between (a) and (b). Further provided are the recombinant host cell and the recombinant cellulose-degrading microorganism comprising the recombinant expression vector, the preparation method and uses thereof.

16 Claims, 3 Drawing Sheets

SEQUENCE LISTING

```
<160> NUMBER OF SEQ ID NOS: 7

<210> SEQ ID NO 1
<211> LENGTH: 1483
<212> TYPE: DNA
<213> ORGANISM: Artificial Sequence
<220> FEATURE:
<223> OTHER INFORMATION: Promoter of Trichoderma reesei
      cellobiohydrolase I

<400> SEQUENCE: 1
gtcggtaatc ccgctgtata gtaatacgag tcgcatctaa atactccgaa gctgctgcga      60
acccggagaa tcgagatgtg ctggaaagct tctagcgagc ggctaaatta gcatgaaagg     120
ctatgagaaa ttctggagac ggcttgttga atcatgcgt tccattcttc gacaagcaaa      180
gcgttccgtc gcagtagcag gcactcattc ccgaaaaaac tcggagattc ctaagtagcg     240
atggaaccgg aataatataa taggcaatac attgagttgc ctcgacggtt gcaatgcagg     300
ggtactgagc ttggacataa ctgttccgta ccccacctct tctcaacctt tggcgtttcc     360
ctgattcagc gtacccgtac aagtcgtaat cactattaac ccagactgac cggacgtgtt     420
ttgcccttca tttggagaaa taatgtcatt gcgatgtgta atttgcctgc ttgaccgact     480
ggggctgttc gaagcccgaa tgtaggattg ttatccgaac tctgctcgta gaggcatgtt     540
gtgaatctgt gtcgggcagg acacgcctcg aaggttcacg gcaagggaaa ccaccgatag     600
cagtgtctag tagcaacctg taaagccgca atgcagcatc actggaaaat acaaaccaat     660
ggctaaaagt acataagtta atgcctaaag gagtcatata ccagcggcta ataattgtac     720
aatcaagtgg ctaaacgtac cgtaatttgc caacggcttg tggggttgca gaagcaacgg     780
caaagcccca cttccccacg tttgtttctt cactcagtcc aatctcagct ggtgatcccc     840
caattgggtc gcttgtttgt tccggtgaag tgaaagaaga cagaggtaag aatgtctgac     900
tcggagcgtt ttgcatacaa ccaagggcag tgatggaaga cagtgaaatg ttgacattca     960
aggagtattt agccagggat gcttgagtgt atcgtgtaag gaggtttgtc tgccgatacg    1020
acgaatactg tatagtcact tctgatgaag tggtccatat tgaaatgtaa gtcggcactg    1080
aacaggcaaa agattgagtt gaaactgcct aagatctcgg gccctcgggc cttcggcctt    1140
tgggtgtaca tgtttgtgct ccgggcaaat gcaaagtgtg gtaggatcga acacactgct    1200
gcctttacca agcagctgag ggtatgtgat aggcaaatgt tcagggcca ctgcatggtt    1260 tcgaatagaa agagaagctt agccaagaac aatagccgat aaagatagcc tcattaaacg    1320
gaatgagcta gtaggcaaag tcagcgaatg tgtatatata aaggttcgag gtccgtgcct    1380
ccctcatgct ctccccatct actcatcaac tcagatcctc caggagactt gtacaccatc    1440
ttttgaggca cagaaaccca atagtcaacc gcggactggc atc                     1483

<210> SEQ ID NO 2
<211> LENGTH: 51
```

```
<212> TYPE: DNA
<213> ORGANISM: Artificial Sequence
<220> FEATURE:
<223> OTHER INFORMATION: Coding sequence of Trichoderma reesei
      cellobiohydrolase I signal peptide

<400> SEQUENCE: 2
atgtatcgga agttggccgt catctcggcc ttcttggcca cagctcgtgc t          51

<210> SEQ ID NO 3
<211> LENGTH: 1220
<212> TYPE: DNA
<213> ORGANISM: Artificial Sequence
<220> FEATURE:
<223> OTHER INFORMATION: F1 fusion fragment coding sequence

<400> SEQUENCE: 3
atgctcttct cttctattgc cattgttgcg gcagcaactg ctgccttggc atcgccggta     60
aagccaagtg ccaagactgc cgcgctatca gtgaagcgtg tctcgaacgt caaatcattg    120
aagaatattg tccaaaaggg ccaagcacgc atcaacaaga tcaatggcgt caaggacatc    180
gaggccagag ctagcggccc agttaccaac gaggatgtta gctatgttgc ctcagtcact    240
atcggtggtc aatcttggga cctcatcgtc gacactggat gtacgtcatc actacataga    300
cactgaacaa cgcatgtgct gacctgatat cctaactagc ttcaaacacg tggtgtggtg    360
cccaacgctc atgcgagcct tcatctactg caagtccac gggcggttcc gtccaggtta     420
gctatggttc cggctccttc tccggcaccg agtacaagga cacagttagc ttcggtggtt    480
tgactgtcac atcacagtcg gttggagctg cccgttcatc ctctggcttt tcaggtgtcg    540
atggaattat tggctttggt ccggtggatc tcactgagga caccgtctcc aacgccaaca    600
cggttccaac cttcctggat aatctctaca gccaaggttc catctcgact gaggtgctgg    660
gtgtttcctt caagccagag tctggcagtg acagcgatga caccaacggc gagttgaccc    720
tcggcggtac tgatagctcc aagtacacgg gctctctcac ctacttctca actctcaaga    780
gtggctctgc tgctccctac tggggcatct ctattgctag tttcacctac ggctcgacga    840
ccctcgcatc gtctgcgacc ggcattgtcg acactggtac tacgctcatc tacatcccca    900
ccaaggctta caatgcattc ctgtctgccg ctggtggcaa gactgacagc tcttctggcc    960
tcgccgtctt ctcaaaagcg ccaacatcca actttgctat caagtttggc tcaacgacct   1020
acacccctca ccttctcaa tacttggttc ccaccgctca gtacagcttc tacggactca    1080
gctctggaaa gtactacgct tggattaacg acggtggcag ctcgggtgtg aacaccatta    1140
ttggtcagaa gttcctggaa aactactact ccgttttga tactaccaac ggccgcatcg     1200
gctttgctac cgcggcttaa                                                1220

<210> SEQ ID NO 4
<211> LENGTH: 48
<212> TYPE: DNA
<213> ORGANISM: Artificial Sequence
<220> FEATURE:
<223> OTHER INFORMATION: linker peptide coding sequence

<400> SEQUENCE: 4
ggatccccag ccactaccac tggaagctct cccggaccta ccacgcgt                 48

<210> SEQ ID NO 5
<211> LENGTH: 2206
<212> TYPE: DNA
<213> ORGANISM: Trichoderma reesei
```

<400> SEQUENCE: 5

```
gttgtacctc ctgcagggac tccatgggga accgcgtacg acaaggcgaa ggccgcattg    60
gcaaagctca atctccaaga taaggtcggc atcgtgagcg tgtcggctg aacggcggt    120
ccttgcgttg gaaacacatc tccggcctcc aagatcagct atccatcgct atgccttcaa   180
gacggacccc tcggtgttcg atactcgaca ggcagcacag cctttacgcc gggcgttcaa   240
gcggcctcga cgtgggatgt caatttgatc cgcgaacgtg gacagttcat cggtgaggag   300
gtgaaggcct cggggattca tgtcatactt ggtcctgtgg ctgggccgct gggaaagact   360
ccgcagggcg gtcgcaactg ggagggcttc ggtgtcgatc catatctcac gggcattgcc   420
atgggtcaaa ccatcaacgg catccagtcg gtaggcgtgc aggcgacagc gaagcactat   480
atcctcaacg agcaggagct caatcgagaa accatttcga gcaacccaga tgaccgaact   540
ctccatgagc tgtatacttg gccatttgcc gacgcggttc aggccaatgt cgcttctgtc   600
atgtgctcgt acaacaaggt caataccacc tgggcctgcg aggatcagta cacgctgcag   660
actgtgctga agaccagct ggggttccca ggctatgtca tgacggactg gaacgcacag   720
cacacgactg tccaaagcgc gaattctggg cttgacatgt caatgcctgg cacagacttc   780
aacggtaaca atcggctctg gggtccagct ctcaccaatg cggtaaatag caatcaggtc   840
cccacgagca gagtcgacga tatggtgact cgtatcctcg ccgcatggta cttgacaggc   900
caggaccagg caggctatcc gtcgttcaac atcagcagaa atgttcaagg aaaccacaag   960
accaatgtca gggcaattgc cagggacggc atcgttctgc tcaagaatga cgccaacatc  1020
ctgccgctca agaagcccgc tagcattgcc gtcgttggat ctgccgcaat cattggtaac  1080
cacgccagaa actcgccctc gtgcaacgac aaaggctgcg acgacggggc cttgggcatg  1140
ggttggggtt ccggcgccgt caactatccg tacttcgtcg cgccctacga tgccatcaat  1200
accagagcgt cttcgcaggg cacccaggtt accttgagca acaccgacaa cacgtcctca  1260
ggcgcatctg cagcaagagg aaaggacgtc gccatcgtct tcatcaccgc cgactcgggt  1320
gaaggctaca tcaccgtgga gggcaacgcg ggcgatcgca caacctgga tccgtggcac  1380
aacggcaatg ccctggtcca ggcggtggcc ggtgccaaca gcaacgtcat tgttgttgtc  1440
cactccgttg gcgccatcat tctggagcag attcttgctc ttccgcaggt caaggccgtt  1500
gtctgggcgg tcttccttc tcaggagagc ggcaatgcgc tcgtcgacgt gctgtgggga  1560
gatgtcagcc cttctggcaa gctggtgtac accattgcga agagccccaa tgactataac  1620
actcgcatcg tttccggcgg cagtgacagc ttcagcgagg gactgttcat cgactataag  1680
cacttcgacg acgccaatat cacgccgcgg tacgagttcg gctatggact gtgtaagttt  1740
gctaacctga caatctatt agacaggttg actgacggat gactgtggaa tgatagctta  1800
caccaagttc aactactcac gcctctccgt cttgtcgacc gccaagtctg gtcctgcgac  1860
tggggccgtt gtgccgggag gcccgagtga tctgttccag aatgtcgcga cagtcaccgt  1920
tgacatcgca aactctggcc aagtgactgg tgccgaggta gcccagctgt acatcaccta  1980
cccatcttca gcacccagga cccctccgaa gcagctgcga ggctttgcca agctgaacct  2040
cacgcctggt cagagcggaa cagcaacgtt caacatccga cgacgagatc tcagctactg  2100
ggacacggct tcgcagaaat gggtggtgcc gtcggggtcg tttggcatca gcgtgggagc  2160
gagcagccgg gatatcaggc tgacgagcac tctgtcggta gcgtaa              2206
```

<210> SEQ ID NO 6

```
<211> LENGTH: 338
<212> TYPE: DNA
<213> ORGANISM: Artificial Sequence
<220> FEATURE:
<223> OTHER INFORMATION: Trichoderma reesei cellobiohydrolase I
      terminator

<400> SEQUENCE: 6
agctccgtgg cgaaagcctg acgcaccggt agattcttgg tgagcccgta tcatgacggc      60
ggcgggagct acatggcccc gggtgattta ttttttttgt atctacttct gaccctttc     120 aaatatacgg tcaactcatc tttcactgga gatgcggcct gcttggtatt gcgatgttgt    180
cagcttggca aattgtggct ttcgaaaaca caaaacgatt ccttagtagc catgcatttt    240
aagataacgg aatagaagaa agaggaaatt aaaaaaaaaa aaaaaacaaa catcccgttc    300 ataaccccgta gaatcgccgc tcttcgtgta tcccagta                           338

<210> SEQ ID NO 7
<211> LENGTH: 1161
<212> TYPE: DNA
<213> ORGANISM: Artificial Sequence
<220> FEATURE:
<223> OTHER INFORMATION: p6281 fusion fragment coding sequence

<400> SEQUENCE: 7
atgctcttct cctctattgc cattgttgcg gcggcaactg ctgccttggc atcgccggta      60
aagccaagtg ccaagactgc cgcgctatca gtgaagcgtg tctcgaacgt caaatcattg    120
aagaatattg tccaaaaggg ccaggcacgc atcaacaaga tcaacggcgt caaagacatc    180
gaggccagag ctagcggccc agccaccaac gaggatgtta gctatgttgc ctcggtcact    240
attggtggta aatcctggga cctcatcgtc gacactggat cttcaaacac gtggtgtggt    300
gctcaaagct catgcgagcc ttcatctact ggcaagtcca cgggcggttc cgtccaggtc    360
agctatggtt ccggctccct ctccggcacc gagtacaagg acacagttag cttcggtggt    420
ttgactgtca catcacagtc ggttggagct gcccgttcat cctctggctt ttcaggtgtc    480
gatggaatta ttggctttgg tccggtggat ctcactgagg acaccgtctc caacgccaac    540
acggttccaa ccttcttgga taatctctac agccaaggtt ccatctcgac tgaggtgctg    600
ggcgtttctt tcaagccaga gtctggcagt gacagtgatg acaccaacgg cgagttgacc    660
ctcggcggta ctgatagctc caagtacacg ggctctctca cctacttctc aactctcaag    720
agtggctctg ctgctcccta ctggggcatc tctattgcta gtttcaccta cggctcgacg    780
accctcgcat cgtctgcgac cggcattgtc gacactggta ctacgctcat ctacatcccc    840
accaaggctt acaatgcatt cctgtctgcc gctggtggca agactgacag ctcttctggc    900
ctcgccgtct tctcaaaagc gccaacatcc aactttgcta tcaagtttgg ctcaacgacc    960 tacacccctca caccttctca atacttggtt cccacctctc agtacagctt ctacggactc   1020
agctctggaa agtactacgc ttggattaac gacggtggca gctcgggtgt caacaccatt   1080
attggccaga agttcctgga aaactactac tccgttttg atactaccaa cggccgcatc    1140
ggctttgcta ccgccgctta a                                             1161
```

METHODS FOR RECOMBINANT EXPRESSION OF BETA-GLUCOSIDASE GENE

This application is a U.S. National Stage Application of PCT Application No. PCT/CN2015/000826, with an international filing date of 27 Nov. 2015. Applicant claims priority based on Chinese Patent Application No. 201410699758.9 filed 27 Nov. 2014.The subject matter of these applications is incorporated herein.

FIELD OF THE INVENTION

The invention relates to the fields of biotechnology and fermentation. In particular, the present invention relates to a method for recombinant expression of β-glucosidase gene from *Trichoderma reesei* via genetic engineering process, microbial strains used in the method and the uses thereof.

BACKGROUND OF THE INVENTION

Cellulose is the main component of plant cell wall, and is a renewable carbon source having the largest amount on the earth. The use of cellulose in the production of fuel ethanol and other chemicals via bioconversion is of extremely important practical significance in the resolution of the energy crisis, food shortages, environmental pollution and other challenges to human beings.

Cellulase, which degrades cellulose, is a multi-enzyme composite system, comprising endoglucanase, exo-cellobiohydrolase and β-glucosidase. These three enzymes act synergistically to degrade cellulose into glucose. Among others, β-glucosidase (EC 3.2.1.21, abbreviated as BGL), could hydrolyze cellobiose to release glucose during the hydrolysis process of cellulose by cellulase, which constitutes the key step of the complete hydrolysis of cellulose.

Generally, there are several issues in the cellulose hydrolysis process as follows. Firstly, the activity of β-glucosidase is inhibited by the hydrolysis product, i.e., glucose, while cellobiose is an inhibitor of the other enzymes in the cellulase system, leading to the inhibition of the whole hydrolysis process of cellulose. Secondly, in cellulase-producing strains, β-glucosidase content is very low (except *Aspergillus niger*). For example, among the cellulases secreted by *T. reesei*, the β-glucosidase content is less than 1%, far less than the level for practical application. Thirdly, the thermal inhibition renders significant loss of β-glucosidase activity during the reaction process. As a result, the activity of β-glucosidase is generally lower than that of endoglucanase and exoglucanase by an order of magnitude or more, becoming the rate-limiting enzyme of cellulose degradation (Wang Zhenyu, et. al., "The activity of the endocellulase and β-glucosidase produced by high temperature anaerobic organism", *Journal of Dalian Institutes of Light Industry*, 2005, 24 (2), 110-114).

Currently, the most widely used cellulase-producing strains are mostly superior mutant strains of *Trichoderma reesei*, which can secret and produce endoglucanase, exoglucanase and β-glucosidase, constituting the whole enzyme system for cellulose hydrolysis (Penttila M. E. et. al., "Expression of two *Trichoderma reesei* Endoglucanase in the Yeast *Saccharomyces cereviae*", *Yeast*. Vol. 3, 1987(3): 175-185).

Due to low β-glucosidase production in natural *T. reesei* strains, the hydrolysis process of cellulose is limited. Therefore, the improvement of β-glucosidase activity in the cellulase system is one of the key measures to improve the yield of cellulase hydrolysis and glucose production.

Some researchers subjected *T. reesei* β-glucosidase gene to recombinant expression in *Pichia* yeasts, and found that the enzyme activity increases along with the duration of induction time, but the fermentation period thereof is up to more than 8 days (Chinese Patent CN102220369B; "Recombinant vector of *Trichoderma reesei* beta-glucosidase gene BGL1, recombinant microorganism, and expression of BGL1 in the recombinant microorganism"). Some researchers over-expressed β-glucosidase in *T. reesei* by fusion expression, and achieved enzyme activity several times higher than that of the original strain, but the fermentation period was up to more than 6 days (Chinese Patent CN 101516906B; "Methods for increasing secretion of polypeptides having biological activity"). Generally, the existing methods are restricted by the disadvantage of overlong fermentation periods.

Therefore, there is an urgent need in the art to develop a cellulose degrading microorganism (for example, genetically engineered *T. reesei*) capable of improving the enzyme activity while shortening the fermentation period, thereby greatly reducing production costs and improving the competitiveness of the cellulase.

BRIEF SUMMARY OF THE INVENTION

The method of the present invention can improve the yield of β-glucosidase enzyme and at the same time shorten the period of enzyme production, address the long fermentation period, low β-glucosidase yield in *T. reesei* and the other deficiencies in the prior art, and thus is of important significances in the improvement of cellulose-degradation efficiency, efficient uses of waste cellulose in energy productions and the resolution of the current energy crisis.

In the first aspect, the present invention provides a fusion protein or coding sequence thereof, the fusion protein comprises:

(a) an aspartic protease or an active fragment thereof;
(b) a β-glucosidase or an active fragment thereof; and
(c) optionally a linker sequence located between (a) and (b), which is, for example, encoded by the sequence as set forth in SEQ ID NO: 4.

In the second aspect, the present invention provides a recombinant expression vector, comprising:

(a) a coding sequence of an aspartic protease or an active fragment thereof;
(b) a coding sequence of a β-glucosidase or an active fragment thereof; and
(c) optionally a coding sequence of a linker sequence located between (a) and (b), which is, for example, the sequence as set forth in SEQ ID NO: 4.

In some embodiments of the present invention, the recombinant expression vector further comprises one or more elements selected from the group consisting of:

(i) a promoter, such as the promoters of *T. reesei* cellobiohydrolase I (CbhI) (e.g., the promoter of the sequence as set forth in SEQ ID NO: 1), *T. reesei* cellobiohydrolase II (CbhII), *T. reesei* endoglucanase I, *T. reesei* endoglucanase II, *T. reesei* endoglucanase III, *T. reesei* endoglucanase IV, *T. reesei* endoglucanase V, *T. reesei* β-xylanase promoter, *T. reesei* β-glucosidase promoter, *Aspergillus oryzae* TATA amylase promoter, *A. oryzae* alkaline protease promoter, *A. oryzae* triose phosphate isomerase, *A. niger* neutral α-amylase promoter, *A. niger* glucoamylase promoter, *Rhizomucor miehei* aspartic protease promoter; in yeast, the useful promoters include: *Saccharomyces cerevisiae* enolase promoter (ENO-1), *S. cerevisiae* galactokinase promoter, *S. cerevisiae* alcohol dehydrogenase promoter/glyceraldehyde-3-phosphate dehydrogenase promoter, *S. cerevisiae* 3-phosphoglycerate kinase promoter;

(ii) a coding sequence of a signal peptide, such as the coding sequences of *T. reesei* cellobiohydrolase I (CbhI) signal peptide (e.g., the coding sequence as set forth in SEQ ID NO: 2), *A. oryzae* amylase signal peptide, *A. niger* glucoamylase signal peptide, *R. miehei* aspartic protease signal peptide;

(iii) a coding sequence of a leader sequence, such as the SD sequence binding to ribosome in prokaryotes to initiate the translation process in prokaryotic expression systems, or the amino acid sequence fused in-frame to the amino terminus of a polypeptide to form a proenzyme or propolypeptide;

(iv) a terminator, such as *T. reesei* cellobiohydrolase I (CbhI) terminator (e.g., the terminator of the sequence as set forth in SEQ ID NO: 6), *A. oryzae* amylase terminator, *A. niger* glucoamylase terminator, *A. nidulans* anthranilate synthase terminator;

(v) a marker gene, such as orotidine-5-phosphate decarboxylase (pyrG), hygromycin phosphotransferase gene (hph), *A. nidulans* acetamidase gene (amdS), ornithine carbamoyl transferase (argB), nitrate reductase (niaD), anthranilate synthase gene (trpC);

(vi) a polyadenylation sequence, e.g., the polyadenylation sequence obtained from the gene of enzymes selected from the group consisting of *A. oryzae* TAKA amylase, *A. niger* glucoamylase, *A. nidulans* anthranilate synthase and *A. niger* α-glucosidase; as well as CCAAT enhancer binding protein (C/EBP)-like factor, GATA transcription factor and the like; and (vii) a transcriptional activator, such as HvCBF2 (C-repeat/DRE binding factor 2) in barley (*Hordeum vulgare*) (Xue et al., 2003).

In some embodiments of the present invention, the basic skeleton of the recombinant expression vector is derived from plasmid pCambia1300, plasmid pCambia3300, plasmid pCambia1301, or plasmid pBin19; preferably, the recombinant expression vector is pAZ193.

In some embodiments of the present invention, the coding sequence of the aspartic protease or active fragment thereof in the above aspect is selected from the group consisting of: the coding sequence of the aspartic protease or active fragment thereof derived from a cellulose-degrading microorganism, e.g. derived from *Trichoderma* (such as *T. harzianum*, *T. reesei*), *Penicillium, Aspergillus, Mucor, Botrytis, Cellulomonas, Cellvibrio, Cytophaga, Bacteroides succinogenes, Ruminococcus flavefaciens, R. albus, Butyrivibrio fibrisolvens*. Preferably, the aspartic protease or active fragment thereof comprises the amino acid sequence encoded by the sequence as set forth in SEQ ID NO: 3 or 7 or the homologous sequence thereof, or the sequence derived from the above amino acid sequences by substitution, deletion or addition of at least one amino acid, preferably the sequences obtained upon conservative substitution of at least one amino acid.

In some embodiments of the present invention, the aspartic protease or active fragment thereof comprises an amino acid sequence with at least 90%, preferably at least 91%, at least 92%, at least 93%, at least 94%, at least 95%, at least 96%, at least 97%, at least 98%, at least 99% homology to the amino acid sequence encoded by the sequence as set forth in SEQ ID NO: 3 or 7, or is encoded by a nucleotide sequence with at least 90%, preferably at least 91%, at least 92%, at least 93%, at least 94%, at least 95%, at least 96%, at least 97%, at least 98%, at least 99% homology to the coding nucleotide sequence as set forth in SEQ ID NO:3 or 7. In preferred embodiments, the aspartic protease is encoded by the coding nucleotide sequence as set forth in SEQ ID NO: 3 or 7. In more preferred embodiments, the aspartic protease comprises or consists of the sequence encoded by sequence as set forth in SEQ ID NO: 3 or 7.

In some embodiments of the present invention, the coding sequence of the β-glucosidase or active fragment thereof in the above aspect is selected from the group consisting of: the coding sequences of the β-glucosidase or active fragment thereof derived from a cellulose-degrading microorganism, e.g. derived from *Trichoderma* (such as *T. harzianum*, *T. reesei*), *Penicillium, Aspergillus* (such as *A. niger, A. oryzae*), *Mucor, Botrytis, Cellulomonas, Cellvibrio, Cytophaga, Bacteroides succinogenes, Ruminococcus flavefaciens, R. albus, Butyrivibrio fibrisolvens*. Preferably, the β-glucosidase or active fragment thereof comprises the amino acid sequence encoded by the sequence as set forth in SEQ ID NO: 5 or the sequences derived from the above amino acid sequence by substitution, deletion or addition of at least one amino acid, preferably the sequences obtained upon conservative substitution of at least one amino acid. Preferably, the coding sequence of the β-glucosidase or active fragment thereof is Bgl1 gene, more preferably the gene is *T. reesei* β-glucosidase Bgl1 gene, e.g., having the sequence as set forth in SEQ ID NO: 5.

In some embodiments of the present invention, the β-glucosidase or active fragment thereof comprises an amino acid sequence with at least 90%, preferably at least 91%, at least 92%, at least 93%, at least 94%, at least 95%, at least 96%, at least 97%, at least 98%, at least 99% homology to the amino acid sequence encoded by the sequence as set forth in SEQ ID NO: 5, or is encoded by a nucleotide sequence with at least 90%, preferably at least 91%, at least 92%, at least 93%, at least 94%, at least 95%, at least 96%, at least 97%, at least 98%, at least 99% homology to the coding nucleotide sequence of the sequence as set forth in SEQ ID NO: 5. In preferred embodiments, the β-glucosidase is encoded by the coding nucleotide sequence of the sequence as set forth in SEQ ID NO: 5. In more preferred embodiments, the β-glucosidase comprises or consists of the sequence encoded by sequence as set forth in SEQ ID NO: 5.

In the third aspect, the present invention provides a recombinant host cell comprising the encoding sequence of the present invention or the recombinant expression vector of the present invention. Preferably, the host cell is *E. coli*, yeast (such as *S. cerevisiae, Pichia* yeast), and *Agrobacterium* (such as *A. tumefaciens* and *A. rhizogenes*).

In the fourth aspect, the present invention provides a recombinant cellulose degrading microorganism, characterized in that the recombinant expression vector of the present invention is transformed into a cellulose degrading microorganism or the host cell of the present invention, thereby recombinantly expressing the coding sequences of the aspartic protease or active fragment thereof and the β-glucosidase or active fragment thereof. Preferably, the cellulose degrading microorganism is derived from *Trichoderma* (such as *T. harzianum, T. reesei*), *Aspergillus* (such as *A. niger, A. oryzae*), *Penicillium*, and more preferably, the cellulose-degrading microorganism is derived from *T. reesei* ATCC56765 or is *T. reesei* ATCC56765.

In some embodiments of the present invention, under the same fermentation conditions, the β-glucosidase activity of the recombinant cellulose degrading microorganism is 2 to 20 times, preferably 3 to 10 times higher than that of the cellulose degrading microorganism without genetic engineering; and/or, the cellulase fermentation period of the recombinant cellulose-degrading microorganism is shorter than that of the cellulose degrading microorganism without genetic engineering. Preferably, the fermentation period lasts for as short as 1 to 3 days for the recombinant cellulose-degrading microorganism.

In the fifth aspect, the present invention provides a method for preparing the recombinant cellulose-degrading microorganism of the invention, the method comprises the steps of:

(i) providing the recombinant expression vector or the recombinant host cell of the present invention;

(ii) transforming a cellulose-degrading microorganism with the recombinant expression vector or the recombinant host under conditions suitable for the transformation, so as to obtain the recombinant cellulose-degrading microorganism of the present invention.

In some embodiments of the invention, the method further comprises (iii) screening, isolating, collecting, culturing, propagating and/or using the transformed cellulose degrading microorganism.

In some embodiments of the invention, the method further comprises screening the recombinant host cell and/or the recombinant cellulose degrading microorganism for the marker gene in the recombinant expression vector.

In some embodiments of the invention, the transformation in step (ii) is carried out by the method selected from the group consisting of Agrobacterium-mediated transformation (such as using A. tumefaciens and A. rhizogenes), gene gun-mediated transformation method, electroporation transformation method, ultrasound-assisted transformation method, in situ transformation method, nuclear microinjection method.

In some embodiments of the invention, the recombinant cellulose-degrading microorganism is used for cellulose degradation directly without isolation, or after isolation, collection, culture and/or propagation.

In the sixth aspect, the invention provides a method for degrading a cellulosic material or cellobiose, the method comprising contacting an effective amount of the fusion protein of the present invention, an effective amount of the recombinant cellulose-degrading microorganism of the present invention and/or an effective amount of the recombinant cellulose-degrading microorganism prepared by the method of the present invention with the cellulosic material or cellobiose under the conditions suitable for degradation of the cellulosic material or cellobiose.

In some embodiments of the invention, the cellulosic material and/or cellobiose has or has not been subjected to pre-treatment (such as isolation, crush, impregnation, enzymatic pretreatment (for example, degraded into cellobiose by enzymatic treatment)) before the contact with the host cell or genetically engineered cellulose degrading microorganism. The degradation is carried out by one or more method(s) selected from the group consisting of solid state fermentation, liquid submerged fermentation, batch fermentation, continuous fermentation and fed batch fermentation.

In some embodiments of the invention, the cellulosic material is selected from the group consisting of agricultural residues, forestry residues, municipal solid wastes, waste paper, and pulp and paper mill residues, such as from wood, corn stalk, cotton, wheat bran, cotton linter, grain, wheat straw, rice straw, reed, hemp, mulberry bark, mulberry bark, bagasse, etc.

In the seventh aspect, the present invention provides a method for recombinant expression of the β-glucosidase or active fragment thereof, the method comprising: providing the recombinant cellulose-degrading microorganism of the invention; expressing the β-glucosidase or active fragment thereof under conditions suitable for expression of the recombinant cellulose-degrading microorganism.

The invention further provides a method for increasing the β-glucosidase yield and shortening the production period of the enzyme, the method comprising a step of producing the β-glucosidase with the recombinant cellulose-degrading microorganism of the invention via fermentation.

Other aspects of the invention will be apparent to those skilled in the art in view of the disclosure herein.

BRIEF DESCRIPTION OF THE DRAWINGS

The present invention is further illustrated below in conjunction with the accompanying drawings, wherein these illustrations are for illustrating the embodiments of the present invention only, but not for limiting the scope of the present invention.

DETAILED DESCRIPTION OF THE INVENTION

Figure 1:
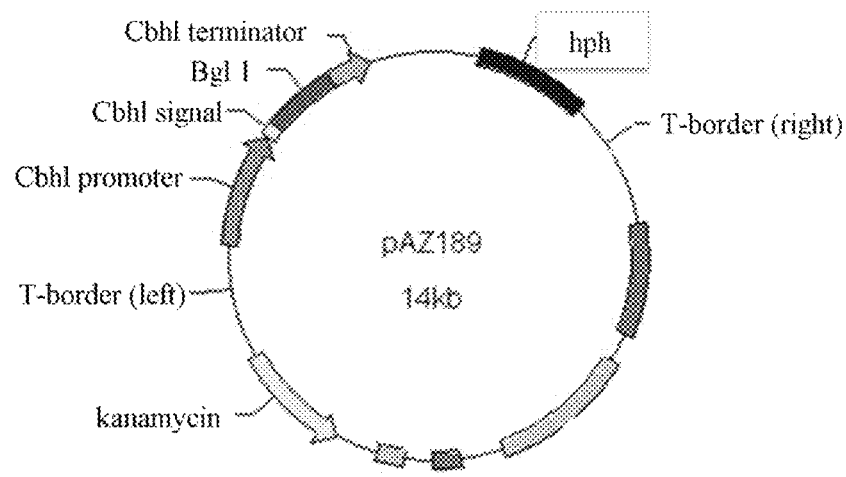
FIG. 1: The construction of expression vector pAZ189, in which hph represents the hygromycin resistance gene.

It has been disclosed in the prior arts that the aspartic protease may influence the expression of heterogenous proteins in recombinant strains (see, for example: MA Ten, Breeding of Aspergillus niger strains overproducing heat-resistant β-glucosidase and gene cloning thereof, master's thesis, Hebei Normal University of Science & Technology, June, 2012; ZHU Huiyuan, Specific gene expression analysis in Aspergillus niger under xylanase inducing conditions and construction of chrysogenum strain over-expressing alkaline xylanase, Shandong University, doctoral dissertation, October, 2010).

However, through long-term and in-depth study, the present inventors have unexpectedly found that: linking the coding sequence of the aspartic protease or active fragment thereof to β-glucosidase Bgl1 gene by genetic engineering manipulations to form an expression vector, and transforming a recombinant microorganism with the resulting expression vector, does not influence the expression of β-glucosidase Bgl1, instead, shortens the fermentation period of the recombinant microorganism, improves its enzyme activity, and significantly improves its degradation of cellulose.

All numerical ranges provided herein are intended to clearly include all numbers falling between the endpoints of the ranges and the numerical ranges therebetween. The features mentioned by the present invention and those mentioned in Examples may be combined. All the features disclosed in the specification can be used in combination with any composition forms, and each feature disclosed in the specification may be replaced with the alternative feature which can be provided for the same, equivalent or similar purpose. Therefore, unless otherwise stated, the disclosed features are only the general examples of the equivalent or similar features.

As used herein, "containing", "having" or "including" includes "comprising", "consisting mainly of . . . ", "consisting essentially of . . . " and "consisting of . . . "; "consisting mainly of . . . ", "consisting essentially of . . . " and "consisting of . . . " belong to the specific concepts of "containing", "having" or "including".

Aspartic Protease or Active Fragments thereof

As used herein, the term "aspartic protease" refers to a class of important proteolytic enzymes, whose active center comprises a catalytic aspartic acid residue.

The aspartic protease of the invention may be: a protein or polypeptide encoded by the sequence as set forth in SEQ ID NO: 3 or 7, a homologous sequence having the similar hydrolytic function as said protein or polypeptide (e.g., a homologous sequence obtained by a database or alignment software known in the art), a variant or a modified form thereof. For example, the aspartic protease may be selected from the group consisting of: (a) an amino acid sequence encoded by the sequence as set forth in SEQ ID NO: 3 or 7; (b) a protein or polypeptide derived from (a) by substitution, deletion or addition of one or more amino acids in the amino acid sequence as defined in (a) and having similar hydrolytic function; or (c) other amino acid sequences having an aspartic protease activity, e.g., the sequence homologous to the sequence encoded by SEQ ID NO: 3 or 7. The aspartic protease of the invention is preferably encoded by the aspartic protease gene or homologous gene or family gene thereof from the cellulose-degrading microorganisms (such as Trichoderma (e.g., T. harzianum, T. reesei).

The variant form of the protein or polypeptide of the invention includes (but is not limited to): deletion, insertion and/or substitution of one or more (generally 1-50, preferably 1-30, more preferably 1-20, most preferably 1-10, e.g., 1, 2, 3, 4, 5, 6, 7, 8, 9 or 10) amino acids, as well as addition of one or more (generally within 20, preferably within 10, more preferably within 5) amino acids at C-terminus and/or N-terminus. For example, it is known in the art that the substitution between amino acids with close or similar property generally would not alter functions of proteins or polypeptides. As another example, the addition of one or several amino acids at C-terminus and/or N-terminus generally would not alter the function of the protein or polypeptide. For example, the aspartic protease of the present invention may or may not include an initial methionine residue while still has proteolytic activity.

The variant form of the polypeptide further comprises: homologous sequence, conservative variant, allelic variant, natural mutant, induced mutant, a protein encoded by a sequence which may hybridize to the aspartic protease coding sequence under high or low stringency conditions.

The aspartic protease or active fragment thereof of the invention comprises an amino acid sequence homologous to the amino acid sequence encoded by the sequence as set forth in SEQ ID NO: 3 or 7, or is encoded by the sequence homologous to the coding nucleotide sequence as set forth in SEQ ID NO: 3 or 7. For example, the aspartic protease or active fragment thereof comprises an amino acid sequence with at least 90%, preferably at least 91%, at least 92%, at least 93%, at least 94%, at least 95%, at least 96%, at least 97%, at least 98%, at least 99% homology to the sequence encoded by the sequence as set forth in SEQ ID NO: 3 or 7, or is encoded by a nucleotide sequence with at least 90%, preferably at least 91%, at least 92%, at least 93%, at least 94%, at least 95%, at least 96%, at least 97%, at least 98%, at least 99% homology to the coding nucleotide sequence as set forth in SEQ ID NO: 3 or 7. In preferred embodiments, the aspartic protease is encoded by the coding nucleotide sequence as set forth in SEQ ID NO: 3 or 7. In more preferred embodiments, the aspartic protease comprises or consists of the amino acid sequence encoded by the sequence as set forth in SEQ ID NO: 3 or 7.

In addition to the nearly full-length polypeptide, the present invention further contemplates a soluble fragment of the aspartic protease, as long as it also has a similar proteolytic activity. Generally, the fragment has at least about 10 contiguous amino acids, generally at least about 30 contiguous amino acids, preferably at least about 50 contiguous amino acids, more preferably at least about 80 contiguous amino acids, most preferably at least about 100 contiguous amino acids of the sequence of the aspartic protease.

Depending on the host used in the recombinant production protocol, the protein or polypeptide of the present invention may be glycosylated or may be non-glycosylated.

The aspartic protease of the present invention further includes the active fragment and active derivative of the aspartic protease, e.g., the variant form and the active fragment of the aspartic protease as described above. Compared with the aspartic protease, the active fragment and active derivative of the aspartic protease has at least 50%, preferably at least 60%, at least 70%, at least 80%, at least 90%, more preferably at least 91%, at least 92%, at least 93%, at least 94%, at least 95%, at least 96%, at least 97%, at least 98%, at least 99%, or 100% of the aspartic protease activity.

The aspartic protease activity can be determined using e.g., modified Anson method, in which:

0.25 ml the sample solution of the enzyme to be determined is mixed with 0.25 ml 1% casein (dissolved in 0.05 M lactic acid-sodium lactate buffer, pH 3.0), and incubated at 40° C. for 10 min. The reaction is then terminated by adding 0.5 ml 10% trichloroacetic acid, and centrifuged at 12,000 g for 5 min. The supernatant is measured for the absorbance at 280 nm.

Definition of activity unit of the enzyme: 1 unit of aspartic protease activity is defined as the amount of the enzyme that hydrolyzes casein in 1 ml liquid to produces 1 microgram tyrosine per minute under the conditions of 0° C. and pH 3.0, and is expressed by U/ml.

Beta-Glucosidase or Active Fragments thereof

As used herein, the term "β-glucosidase" refers to an important component in the cellulolytic enzyme system, which is capable of hydrolyzing the non-reducing β-D-glucoside from the terminus, while releasing β-D-glucose and the corresponding ligand.

The β-glucosidase of the invention may be: a protein or polypeptide encoded by the sequence as set forth in SEQ ID NO: 5, a homologous sequence having the similar hydrolytic function as said protein or polypeptide (e.g., a homologous sequence obtained by a database or alignment software known in the art), a variant or a modified form thereof. For example, the β-glucosidase may be selected from the group consisting of: (a) an amino acid sequence encoded by the sequence as set forth in SEQ ID NO: 5; (b) a protein or polypeptide derived from (a) by substitution, deletion or addition of one or more amino acids in the amino acid sequence as defined in (a) and having β-glucosidase activity; or (c) other amino acid sequences having β-glucosidase activity, e.g., the sequence homologous to the sequence encoded by SEQ ID NO: 5. The β-glucosidase of the invention is preferably encoded by the β-glucosidase gene or homologous gene or family gene thereof from the cellulose-degrading microorganism (such as Trichoderma (e.g., *T. harzianum*, *T. reesei*).

The variant form of the protein or polypeptide of the invention includes (but is not limited to): deletion, insertion and/or substitution of one or more (generally 1-50, preferably 1-30, more preferably 1-20, most preferably 1-10, e.g., 1, 2, 3, 4, 5, 6, 7, 8, 9 or 10) amino acids, as well as addition of one or more (generally within 20, preferably within 10, more preferably within 5) amino acids at C-terminus and/or N-terminus. For example, it is known in the art that the substitution between amino acids with close or similar property generally would not alter functions of proteins or polypeptides. As another example, the addition of one or several amino acids at C-terminus and/or N-terminus generally would not alter the function of the protein or polypeptide. For example, the β-glucosidase of the present invention may or may not include an initial methionine residue while still has β-glucosidase activity.

The variant form of the polypeptide further comprises: homologous sequence, conservative variant, allelic variant, natural mutant, induced mutant, a protein encoded by a sequence which may hybridize to the β-glucosidase coding sequence under high or low stringency conditions.

The β-glucosidase or active fragment thereof of the invention comprises an amino acid sequence homologous to the sequence encoded by the sequence as set forth in SEQ ID NO: 5, or is encoded by the sequence homologous to the coding nucleotide sequence of the sequence as set forth in SEQ ID NO: 5. For example, the β-glucosidase or active fragment thereof comprises an amino acid sequence with at least 90%, preferably at least 91%, at least 92%, at least 93%, at least 94%, at least 95%, at least 96%, at least 97%, at least 98%, at least 99% homology to the sequence encoded by the sequence as set forth in SEQ ID NO: 5, or is encoded by a nucleotide sequence with at least 90%, preferably at least 91%, at least 92%, at least 93%, at least 94%, at least 95%, at least 96%, at least 97%, at least 98%, at least 99% homology to the coding nucleotide sequence as set forth in SEQ ID NO: 5. In preferred embodiments, the β-glucosidase is encoded by the coding nucleotide sequence as set forth in SEQ ID NO: 5. In more preferred embodiments, the aspartic protease comprises or consists of the sequence encoded by the sequence as set forth in SEQ ID NO: 5.

In addition to the nearly full-length polypeptide, the present invention further contemplates a soluble fragment of the β-glucosidase, as long as it also has a similar β-glucosidase activity. Generally, the fragment has at least about 10 contiguous amino acids, generally at least about 30 contiguous amino acids, preferably at least about 50 contiguous amino acids, more preferably at least about 80 contiguous amino acids, most preferably at least about 100 contiguous amino acids of the sequence of the β-glucosidase.

Depending on the host used in the recombinant production protocol, the protein or polypeptide of the present invention may be glycosylated or may be non-glycosylated.

The β-glucosidase of the present invention further comprises the active fragment and active derivative of the β-glucosidase, e.g. the variant form and the active fragment of the β-glucosidase as described above. Compared with the β-glucosidase, the active fragment and active derivative of the β-glucosidase has at least 50%, preferably at least 60%, at least 70%, at least 80%, at least 90%, more preferably at least 91%, at least 92%, at least 93%, at least 94%, at least 95%, at least 96%, at least 97%, at least 98%, at least 99%, or 100% of the β-glucosidase activity. The β-glucosidase activity is measured by the method as described by e.g., Venturi et al., Extracellular β-D-glucosidase from *Chaetomium thermophilum* var. *coprophilum*: production, purification and some biochemical properties, *J. Basic Microbiol.* 2002(42): 55-66.

Coding Sequence

As used herein, the terms "gene", "coding sequence" or "protein/polypeptide coding sequence" are used interchangeably, and all refer to a sequence encoding the desired protein or polypeptide or active fragment thereof of the invention (e.g. aspartic protease or active fragment thereof, β-glucosidase or active fragment thereof).

For the aspartic protease or active fragment thereof, the coding sequence thereof may be e.g., the nucleotide sequence as set forth in SEQ ID NO: 3 or 7, the molecule hybridized to these sequences under stringent conditions, or the family gene molecule highly homologous to the above molecules, wherein the expression of the gene can produce the aspartic protease or active fragment thereof, which is fused to the β-glucosidase or active fragment thereof. For example, the coding sequence of the aspartic protease of the present invention may be selected from the group consisting of: (i) the nucleotide sequence as set forth in SEQ ID NO: 3 or 7; or (ii) the molecules hybridized to the sequence as defined in (i) under stringent conditions and encoding a polypeptide having aspartic protease activity.

For the β-glucosidase or active fragment thereof, the coding sequence thereof may be e.g., *T. reesei* Bfl1 sequence as set forth in SEQ ID NO: 5, the molecule hybridized to these sequences under stringent conditions, or the family gene molecule highly homologous to the above molecules, wherein the expression of the gene can produce the β-glucosidase or active fragment thereof, which is fused to the aspartic protease or active fragment thereof. For example, the coding sequence of the β-glucosidase of the invention may be selected from the group consisting of: (i) the nucleotide sequence as set forth in SEQ ID NO: 5; or (ii) the molecule hybridized to the sequence as defined in (i) under a stringent condition and encoding a polypeptide having β-glucosidase activity.

The coding sequence of the fusion fragment of the invention may comprise at least one copy (e.g., 1 to 20 copies, 1 to 10 copies, etc.) of the coding sequence of the aspartic protease or active fragment thereof and at least one copy (e.g., 1 to 20 copies, 1 to 10 copies, etc.) of the coding sequence of β-glucosidase Bgl1 or active fragment thereof.

In the coding sequence of the fusion fragment of the present invention, the coding sequence of the aspartic protease or active fragment thereof may be located upstream or downstream of the coding sequence of the β-glucosidase Bgl1 or active fragment thereof.

As used herein, the term "stringent condition" refers to: (1) hybridization and washing processes at lower ionic strengths and higher temperatures, such as, 0.2×SSC, 0.1% SDS, 60° C.; or (2) hybridization with denaturant added, such as, 50% (v/v) formamide, 0.1% calf serum/0.1% Ficoll, 42° C., etc.; or (3) hybridization occurred only when the identity between two sequences is at least 50%, preferably 55% or above, 60% or above, 65% or above, 70% or above, 75% or above, 80% or above, 85% or above, or 90% or above, more preferably 95% or above. For example, the sequence may be the sequence complementary to the sequence as defined in (a).

The full length sequence or fragment thereof of the coding sequence of the invention can generally be obtained via PCR amplification, recombination or artificial synthesis methods. For the PCR amplification method, primers can be designed according to the relevant nucleotide sequences disclosed in the invention, especially the open reading frame sequences, and used in amplification using a commercially available cDNA library or cDNA library prepared by conventional methods known to those skilled in the art as templates to produce related sequences. For longer sequence, it usually requires to perform two or more PCR amplifications, and then ligate each amplified fragments together in a correct order.

The coding sequences of the invention are preferably derived from cellulose degrading microorganisms. The other genes derived from the other microorganisms and having high identity (such as a sequence identity of 50% or higher, preferably 55% or higher, 60% or higher, 65% or higher, 70% or higher, 75% or higher, 80% or higher, more preferably 85% or higher, such as 85%, 90%, 95%, 98% or even 99% or higher) with the corresponding coding sequence in the cellulose-degrading microorganisms are also within the equivalent scope preferably contemplated in the present invention. The methods and tools for sequence alignment and calculating the similarity therebetween are also well known in the art, such as BLAST with default parameters thereof.

Recombinant Expression Vector, Recombinant Expression Host and Recombinant Cellulose-Degrading Microorganism The present invention relates to a recombinant expression vector comprising the coding sequence of the aspartic protease or active fragment thereof and the coding sequence of the β-glucosidase or active fragment thereof, a host cell comprising the recombinant expression vector, and a recombinant cellulose degrading microorganism obtained by transformation.

By conventional recombinant DNA technique (Science, 1984; 224: 1431), the coding sequence of the present invention may be used to express or produce the recombinant protein. For example, it may comprise the following steps:

(1) transforming or transducing a suitable host cell with the recombinant expression vector of the invention, and transforming the cellulose degrading microorganism with the host cell; or directly transforming the target strain (e.g., the cellulose-degrading microorganism) with the recombinant expression vector of the present invention to obtain a recombinant cellulose-degrading microorganism;

(2) isolating, collecting, culturing, propagating and/or using the recombinant cellulose degrading microorganism directly or indirectly transformed with the recombinant expression vector.

In the present invention, the terms "vector" and "recombinant expression vector" may be used interchangeably, and refer to bacterial plasmid, bacteriophage, yeast plasmid, cellular virus or other vectors well known in the art. In short, any plasmids and vectors can be used, as long as they can replicate and be stable in the host. As an important feature, the expression vector typically contains an origin of replication, a promoter, a marker gene and a translation control element.

The methods well known to those skilled in the art can be used to construct an expression vector containing the coding sequence of the aspartic protease or active fragment thereof and the coding sequence of the β-glucosidase or active fragment thereof, and appropriate transcriptional/translational control signals. These methods include in vitro recombinant DNA technique, DNA synthesis technique, in vivo recombination technique and the like. The DNA sequence can be operably linked to an appropriate promoter in the expression vector to direct mRNA synthesis. The expression vector further includes a ribosome binding site for translation initiation and a transcription terminator. The present invention preferably uses cbhI promoter, cbhI promoter vector, and *T. reesei* expression system.

In addition, the expression vector preferably comprises one or more selectable marker genes to provide a phenotypic trait for selection of transformed host cells, such as hygromycin resistance gene for hygromycin-screening process, dihydrofolate reductase, neomycin resistance, and green fluorescent protein (GFP) for eukaryotic cell culture, or tetracycline or ampicillin resistance for *E. coli*.

A vector comprising the above appropriate DNA sequences and appropriate promoter or control sequences may be used for transforming an appropriate host cell, which may be used in turn for transforming an appropriate target microorganism to endow the target microorganism with a desired cellulose degrading activity. The host cell can be a prokaryotic cell, such as a bacterial cell; or a lower eukaryotic cell, such as a yeast cell. The representative examples include: *E. coli, Streptomyces* spp., *Agrobacterium* spp. (such as *A. tumefaciens* and *A. rhizogenes*); fungal cells, such as yeast and the like. In the present invention, it is preferable to use *Agrobacterium* (e.g., *A. tumefaciens* and *A. rhizogenes*) as a host cell. Those ordinarily skilled in the art all know how to choose the appropriate vector, promoter, enhancer, and host cell.

In the present invention, the term "recombinant cellulose-degrading microorganism" refers to a microorganism transformed with the coding sequence of the aspartic protease or active fragment thereof and the coding sequence of the β-glucosidase or active fragment thereof, and stably expressing the proteins or polypeptides, preferably the "cellulose-degrading microorganism" itself possesses the cellulose-degrading activity.

In the above method, the recombinant polypeptide can be expressed intracellularly or on the membrane or secreted outside of the cell. If desired, the recombinant protein can be isolated and purified by various isolation methods according to its physical, chemical, and other properties. These methods are well known to those skilled in the art. Examples of such methods include, but are not limited to: conventional renaturation treatment, treatment with protein precipitants (salting out method), centrifugation, osmotic lysis, ultrasonic treatment, ultracentrifugation, molecular sieve chromatography (gel filtration), adsorption chromatography, ion exchange chromatography, high performance liquid chromatography (HPLC) and other various liquid chromatographic techniques and the combination thereof.

Cellulose Degrading Activity

As used herein, the term "cellulosic material" refers to any cellulose-containing material. Typically, cellulose can be found in e.g., stem, leaf, shell, bark and cob of plants or leaf, branch, and xylem of trees. Cellulosic material can also be, but not limited to, herbaceous material, agricultural residue, forestry residue, municipal solid waste, waste paper, and pulp and paper mill residue. It should be appreciated that the cellulose herein may be in the form of lignocellulose, i.e., plant cell wall materials containing lignin, cellulose, and hemicellulose in a mixed matrix.

In a preferred aspect, the cellulosic material is corn stalks. In another preferred aspect, the cellulosic material is corn fiber. In another preferred aspect, the cellulosic material is rice straw. In another preferred aspect, the cellulosic material is paper and pulp processing waste. In another preferred aspect, the cellulosic material is woody or herbaceous plant. In another preferred aspect, the cellulosic material is bagasse.

The cellulosic material can be used via conventional methods known in the art. The cellulosic material is pretreated or may be pretreated. For example, physical pretreatment techniques can include various types of milling, irradiation, steaming/steam explosion, and wet-heat decomposition; chemical pretreatment techniques can include uses of diluted acids, alkali, organic solvents, ammonia, sulfur dioxide, carbon dioxide, and pH-controlled wet-heat decomposition; and biological pretreatment techniques can include uses of lignin-degrading microorganisms.

Herein, the term "fermentation" refers to the process of degrading a cellulosic material or the derivative thereof (such as cellobiose) using the recombinant cellulose-degrading microorganism of the present invention. The process can be performed using the conventional fermentation equipment and technology in the art, and the equipment and technology can be selected by those of ordinary skill according to the actual needs and conditions.

As used herein, the term "cellulose-degrading activity" refers to the biological activity of hydrolyzing cellulose materials, mainly involves, among others, the enzyme amount and/or activity of the rate-limiting enzyme of the cellulose degradation process (i.e., β-glucosidase), duration of the fermentation period and the like. The term "improved cellulose-degrading activity" means that the genetically engineered cellulose-degrading microorganism has more β-glucosidase, higher activity of β-glucosidase, and/or shorter fermentation period, compared with the cellulose degrading microorganism without genetic engineering.

For example, in some embodiments of the present invention, the β-glucosidase activity of the recombinant cellulose-degrading microorganism is 2 to 20 times, preferably 3 to 10 times higher than that of the cellulose-degrading microorganism without genetic engineering; and/or, the cellulose-degrading fermentation period of the recombinant cellulose-degrading microorganism is shorter than that of the cellulose degrading microorganism without genetic engineering. Preferably the cellulose degrading fermentation period of the recombinant cellulose-degrading microorganism of the present invention is as short as 1 to 3 days.

As used herein, "the cellulose-degrading microorganism without genetic engineering" refers to a cellulose degrading microorganism otherwise the same as the recombinant cellulose degrading microorganism of the present invention, except that it has not been subjected to transformation with the recombinant expression vector of the present invention. The cellulose degrading microorganism can be or be derived from *Trichoderma reesei* ATCC56765 or *Trichoderma reesei* ATCC56765, but not limited thereto.

The Exemplary Embodiments of the Present Invention

The following is an exemplary embodiment of the present invention. It should be understood that all the features disclosed therein can be used in combination with the other forms of the present invention, and each feature disclosed therein may be replaced with the alternative feature which can be provided for the same, equivalent or similar purpose. Therefore, unless otherwise stated, the disclosed features are merely the general examples of the equivalent or similar features.

A. Sources of Fusion Fragments

As used herein, the term "fusion fragment" refers to a fusion product of aspartic protease or active fragment thereof and β-glucosidase Bgl1 or active fragment thereof.

The aspartic protease in the fusion fragment can be, for example: the aspartic protease encoded by p6281 gene (SEQ ID NO: 7) in the NCBI database, or the aspartic protease encoded by the sequence F1 (SEQ ID NO: 3), which has 99% sequence identity with the coding sequence of p6281 gene.

The fusion fragment of the invention may comprise at least one copy (e.g., 1 to 20 copies, 1 to 10 copies, etc.) of the aspartic protease or active fragment thereof and the β-glucosidase Bgl1 or active fragment thereof. Accordingly, the coding sequence of the fusion fragment of the present invention may comprise at least one copy (e.g., 1 to 20 copies, 1 to 10 copies, etc.) of the coding sequence.

In the fusion fragment of the present invention, the aspartic protease or active fragment thereof may be located upstream or downstream of the β-glucosidase Bgl1 or active fragment thereof. Accordingly, in the coding sequence of the fusion fragment of the present invention, the coding sequence of the aspartic protease or active fragment thereof may be located upstream or downstream of the coding sequence of the β-glucosidase Bgl1 or active fragment thereof.

B. Construction of *Trichoderma reesei* BGL1 Expression Vector

Following the method described in "Molecular Cloning, A Laboratory Manual" (third edition, Academic Press, 2002, [US] edited by J. Sambrook, et. al., and translated by Peitang HUANG), based on pCambia1300 (commercially available from Invitrogen), CbhI promoter, CbhI signal peptide, Bgl1 gene and CbhI terminator are sequentially inserted into the multiple cloning site. The expression vector pAZ189 as shown in FIG. 1 is constructed, which comprises: CbhI promoter, CbhI signal peptide, Bgl1 gene, and CbhI terminator.

Figure 2:
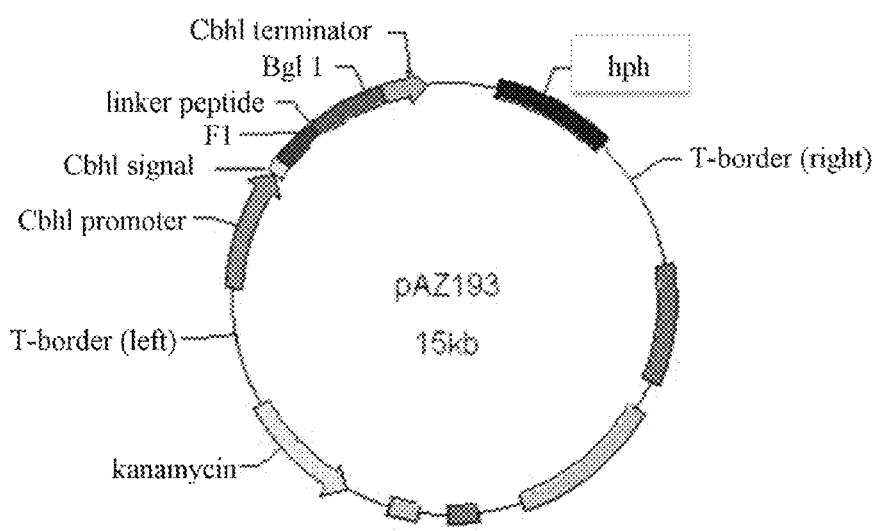
FIG. 2: The construction of fusion expression vector pAZ193, in which hph represents the hygromycin resistance gene.

Following the method described in "Molecular Cloning, A Laboratory Manual" (third edition, Academic Press, 2002, [US] edited by J. Sambrook, et. al., and translated by Peitang HUANG), based on pCambia1300 (commercially available from Invitrogen), CbhI promoter, CbhI signal peptide, F1 fusion fragment, linker peptide, Bgl1 gene and CbhI terminator are sequentially inserted into the multiple cloning site. The pAZ193 expression vector as shown in FIG. 2 is constructed, which comprises: CbhI promoter, CbhI signal peptide, F1 fusion fragment, linker peptide, Bgl1 gene, and CbhI terminator.

Figure 3:
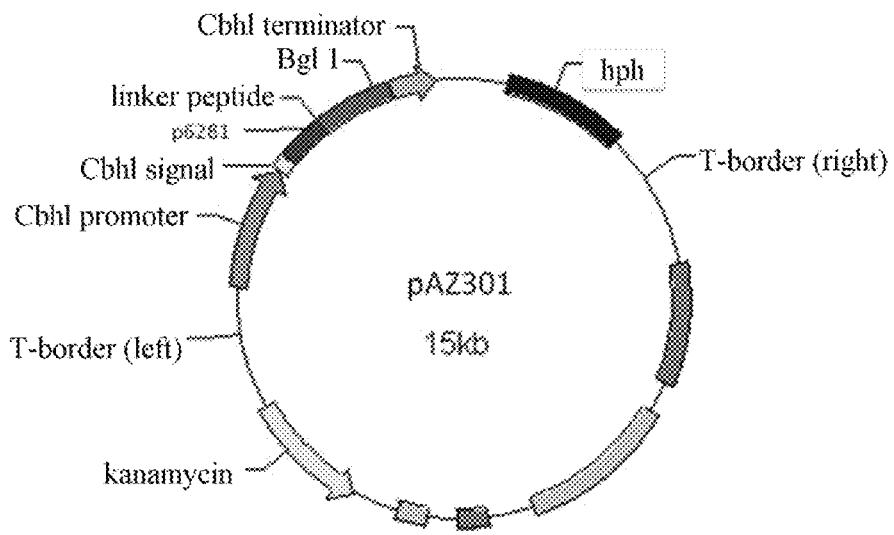
FIG. 3: The construction of expression vector pAZ301, in which hph represents the hygromycin resistance gene.

Following the method described in "Molecular Cloning, A Laboratory Manual" (third edition, Academic Press, 2002, [US] edited by J. Sambrook, et. al., and translated by Peitang HUANG), based on pCambia1300 (commercially available from Invitrogen), CbhI promoter, CbhI signal peptide, p6281 fusion fragment, linker peptide, Bgl1 gene and CbhI terminator are sequentially inserted into the multiple cloning site. The pAZ301 expression vector as shown in FIG. 3 is constructed, which comprises: CbhI promoter, CbhI signal peptide, p6281 fusion fragment, linker peptide, Bgl1 gene, and CbhI terminator.

C. Transformation of *Trichoderma reesei* RUT-C30 with Expression Vectors pAZ189, pAZ193 and pAZ301

*Trichoderma reesei* (particularly RUT-C30, commercially available from ATCC, i.e., ATCC56765) is transformed via *Agrobacterium tumefaciens* transformation method. The specific method makes reference to de Groot, M. J. et al., *Agrobacterium tumefaciens*-mediated transformation of filamentous fungi. *Nature Biotechnology*, 1998(16): 839-842.

D. Screening and Enzyme Activity Assay on Transformants of pAZ193, pAZ189 or pAZ301 Expression Vectors The specific method makes reference to de Groot, M. J. et al., *Agrobacterium tumefaciens*-mediated transformation of filamentous fungi. *Nature Biotechnology*, 1998(16): 839-842.

Enzyme Activity Assay: β-glucosidase activity is the activity of β-D-glucoside glucohydrolase (EC3.2.1.21), which catalyzes the hydrolysis of the terminal non-reducing β-D-glucose residue, while releasing β-D-glucose at the same time. The β-glucosidase activity was determined according to the procedure as described by Venturi, et al., (Extracellular β-D-glucosidase from *Chaetomium thermophilum* var. *coprophilum*: production, purification and some biochemical properties, *J. Basic Microbiol.* 2002(42): 55-66).

One unit of enzyme activity of the glucosidase is defined as the amount of enzyme that produces 1.0 μM p-nitrophenol per minute from the substrate of 4 mM p-nitrophenyl-β-D-glucopyranoside in 100 mM sodium citrate with 0.01% TWEEN® 20 under the conditions of 50° C. and pH 5.

Advantages of the Present Invention

The recombinant cellulose-degrading microorganism of the present invention can efficiently express β-glucosidase in a shorter fermentation period (fermentation period of only 1 to 3 days) with an enzyme activity significantly higher than the original strain, thereby overcoming the deficiencies of low expression level of β-glucosidase fermentation in *T. reesei* and long period for enzyme production (fermentation period up to 5 to 8 days) in the prior art.

Sequence Listing

The sequence ID number and the corresponding sequence name of each sequence are shown in the following table:

| SEQ ID NO: | Sequence name |
| --- | --- |
| 1 | CbhI promoter sequence |
| 2 | A signal peptide coding sequence |
| 3 | F1 coding sequence |
| 4 | A linker peptide coding sequence |
| 5 | *Trichoderma reesei* Bgl1 sequence |
| 6 | CbhI terminator sequence |
| 7 | p6281 coding sequence |

EXAMPLES

The present invention will be further illustrated hereinafter in conjunction with the specific examples. It should be understood that these examples are merely illustrative of the present invention and are not intended to limit the scope of the invention. Those skilled in the art can make appropriate modifications and variations to the present invention, which are all within the scope of the present invention.

In the following examples, the conventional methods in the art, or the conditions recommended by the supplier may be utilized for the experimental process, for which the specific conditions are not indicated. The references can be made to such as, "Molecular Cloning, A Laboratory Manual" (third edition, New York: Cold Spring Harbor Laboratory Press, 1989), and "Experiment Textbook of Biochemistry and Molecular Biology" (Edited by Songping LIANG, Higher Education Press). The DNA sequencing methods are the conventional methods in the art, or provided by commercial companies.

Unless otherwise stated, percentages and parts are calculated by weight. Unless otherwise defined, the meanings of all professional and scientific terminology used herein are same as those familiar to those skilled in the art. In addition, the methods and materials that are similar or equivalent to the present disclosure are all applicable to the methods of the invention. The preferred embodied methods and materials are for exemplary purpose only.

Example 1

Sources of the β-Glucosidase

*Trichoderma reesei* RUT-C30 (purchased from ATCC, i.e. ATCC56765) was used to express β-glucosidase. RUT-C30 was cultured at 30° C. for 5-7 days. The spore plates were then washed with 0.8% physiological saline. The spore suspension was collected, and then inoculated into 50 ml cellulase-inducing medium in 250 ml glass shake flasks. The composition of the medium is as follows:

$(NH4)_2SO_4$ 5 g/L; MES buffer 19.52 g/L; yeast extract (OXOID, Cat. No. LP0021) 9 g/L; $KH_2PO_4$ 4.5 g/L; $CaCl_2.2H_2O$ 1.32 g/L; $MgSO_4.7H_2O$ 1 g/L; defoamer (purchased from Nanjing Huaxing Defoamers Co.; Cat. No. xp-m-130) 5 ml/L, 400× trace elements 2.5 ml/L pH 5.5; lactose (sterilized separately) 40 g/L, wherein, the solutions of 400× trace elements are: citric acid (anhydrous) 175 g/L; $FeSO_4.7H_2O$ 200 g/L; $ZnSO_4.7H_2O$ 16 g/L; $CuSO_4.5H_2O$ 3.2 g/L; $MnSO_4.4H_2O$ 1.4 g/L; $H_3BO_3$ 0.8 g/L.

The culture was incubated at 30° C. with shaking at a constant speed of 200 rpm. From the day next to the start of fermentation, 1 ml fermentation culture was taken on Days 2, 3, 4, and 6, centrifuged at 12000×g, and the supernatant was collected.

Example 2

Sources of the Sequence Fragment Encoding the Aspartic Protease

The encoding sequences of the aspartic protease for construction of the fusion protein expression vector are respectively as follows: (1) sequence F1, synthesized by Sangon Bioengineering (Shanghai) Ltd., having 99% identity with the p6281 gene in the NCBI database; (2) p6281 gene from the NCBI database, synthesized by Sangon Bioengineering (Shanghai) Ltd.

Example 3

Construction of Expression Vector pAZ189 of *Trichoderma reesei* β-Glucosidase Gene Following the method described in "Molecular Cloning, A Laboratory Manual" (third edition, Academic Press, 2002, [US] edited by J. Sambrook, et. al., and translated by Peitang HUANG), based on pCambia1300 (purchased from Invitrogen), CbhI promoter (SEQ ID NO: 1), CbhI signal peptide coding sequence (SEQ ID NO: 2), Bgl1 gene (SEQ ID NO: 5) and CbhI terminator (SEQ ID NO: 6) were sequentially inserted into the multiple cloning site to construct the expression vector pAZ189 of *Trichoderma reesei* β-glucosidase gene.

The expression vector comprises the following sequences: CbhI promoter, CbhI signal peptide coding sequence, Bgl1 gene, and CbhI terminator. The specific structure of the vector is shown in FIG. 1.

Example 4

Construction of Expression Vector pAZ193 of *Trichoderma reesei* β-Glucosidase Gene Following the method described in "Molecular Cloning, A Laboratory Manual" (third edition, Academic Press, 2002, [US] edited by J. Sambrook, et. al., and translated by Peitang HUANG), based on pCambia1300 (purchased from Invitrogen), CbhI promoter (SEQ ID NO: 1), CbhI signal peptide coding sequence (SEQ ID NO: 2), F1 fusion fragment coding sequence (SEQ ID NO: 3), linker peptide coding sequence (SEQ ID NO: 4), Bgl1 gene (SEQ ID NO: 5), and CbhI terminator (SEQ ID NO: 6) were sequentially inserted into the multiple cloning site to construct the expression vector pAZ193 of *Trichoderma reesei* β-glucosidase gene.

The expression vector comprises: CbhI promoter, CbhI signal peptide coding sequence, F1 fusion fragment coding sequence, linker peptide coding sequence, Bgl1 gene, and CbhI terminator. The specific structure of the vector is shown in FIG. 2.

Example 5

Construction of Expression Vector pAZ301 of *Trichoderma reesei* β-Glucosidase Gene Following the method described in "Molecular Cloning, A Laboratory Manual" (third edition, Academic Press, 2002, [US] edited by J. Sambrook, et. al. and translated by Peitang HUANG), based on pCambia1300 (purchased from Invitrogen), CbhI promoter (SEQ ID NO: 1), CbhI signal peptide coding sequence (SEQ ID NO: 2), p6281 fusion fragment coding sequence (SEQ ID NO: 7), linker peptide coding sequence (SEQ ID NO: 4), Bgl1 gene (SEQ ID NO: 5), and CbhI terminator (SEQ ID NO: 6) were sequentially inserted into the multiple cloning site to construct the expression vector pAZ301 of *Trichoderma reesei* β-glucosidase gene.

The expression vector comprises: CbhI promoter, CbhI signal peptide coding sequence, p6281 fusion fragment coding sequence, linker peptide coding sequence, Bgl1 gene, and CbhI terminator. The specific structure of the vector is shown in FIG. 3.

Example 6

Transformation of *Trichoderma reesei* RUT-C30 with the β-Glucosidase Expression Vector pAZ189

The expression vector pAZ189 was introduced into *Trichoderma reesei* RUT-C30 strain by *Agrobacterium tumefaciens* AGL1 (purchased from Invitrogen)-mediated transformation. The specific method makes reference to de Groot, M. J., *Agrobacterium tumefaciens*-mediated transformation of filamentous fungi, Nature Biotechnology, 1998 (16): 839-842). About 200 transformants were obtained in total.

Example 7

Transformation of *Trichoderma reesei* RUT-C30 with the β-Glucosidase Expression Vector pAZ193

The expression vector pAZ193 was introduced into *Trichoderma reesei* RUT-C30 strain by *Agrobacterium tumefaciens* AGL1-mediated transformation. The specific method makes reference to de Groot, M. J., Bundock, P., Hooykaas, P. J., Beijersbergen, A. G. 1998. *Agrobacterium tumefaciens*-mediated transformation of filamentous fungi. Nature Biotechnology 16, 839-842. About 500 transformants were obtained in total.

Example 8

Transformation of *Trichoderma reesei* RUT-C30 with the β-Glucosidase Expression Vector pAZ301

The expression vector pAZ301 was introduced into *Trichoderma reesei* RUT-C30 by *Agrobacterium tumefaciens* AGL1-mediated transformation. The specific method makes reference to de Groot, M. J., Bundock, P., Hooykaas, P. J., Beijersbergen, A. G. 1998. *Agrobacterium tumefaciens*-mediated transformation of filamentous fungi. Nature Biotechnology 16, 839-842. About 200 transformants were obtained in total.

Example 9

Screening of *Trichoderma reesei* Transformants of pAZ189 and Detection of Enzyme Activity The primary screening of the transformants obtained in example 6 was carried out on screening plates for hygromycin resistance, and the composition of the medium is as follows (g/L):

Dipotassium phosphate ($K_2HPO_4$) 2.05 g/L; potassium dihydrogen phosphate ($KH_2PO_4$) 1.45 g/L; sodium chloride (NaCl) 0.15 g/L; magnesium sulfate heptahydrate ($MgSO_4.7H_2O$) 0.5 g/L; calcium chloride hexahydrate ($CaCl_2.6H_2O$) 0.1 g/L; ferrous sulfate heptahydrate ($FeSO_4.7H_2O$) 0.0025 g/L; ammonium sulfate $(NH_4)_2SO_4$ 0.5 g/L; glucose 2 g/L; Hygromycin 10 mg/L.

For the screening hygromycin resistant transformants, the particular method makes reference to de Groot, M. J. et al, *Agrobacterium tumefaciens*-mediated transformation of filamentous fungi. Nature Biotechnology, 1998(16): 839-842.

After the primary screening, the spores were collected from the transformants for the fermentation for the enzyme production (referring to Chinese Patent Application CN200980107269 ("Over-expression of catalase in *Trichoderma*") for the fermentation conditions for the *T. reesei* transformants). The spore-plates of nine transformants were taken randomly, and washed with 3 ml 0.01% TWEEN® 80. In particular, several transformants were picked after primary screening; each transformant was individually inoculated onto hygromycin selection medium, and cultured at 30° C. for 5-7 days. Then, the plates were washed with 0.8% normal saline and the spores were collected into the suspension. The spores were inoculated into 50 ml cellulase-inducing medium in 250 ml glass shake flasks. The composition of the medium is as follows:

$(NH4)_2SO_4$ 5 g/L; MES buffer 19.52 g/L; yeast extract (Yeast Extract, OXOID, Cat. No. LP0021) 9 g/L; $KH_2PO_4$ 4.5 g/L; $CaCl_2.2H_2O$ 1.32 g/L; $MgSO_4.7H_2O$ 1 g/L; defoamer (purchased from Nanjing Huaxing Defoamers Co.; Cat. No. xp-m-130) 5 ml/L; 400× trace elements 2.5 ml/L pH 5.5; lactose (sterilized separately) 40 g/L, wherein, the solutions of 400× trace elements are: citric acid (anhydrous) 175 g/L; $FeSO_4.7H_2O$ 200 g/L; $ZnSO_4.7H_2O$ 16/L; $CuSO_4.5H_2O$ 3.2 g/L; $MnSO_4.4H_2O$ 1.4 g/L; $H_3BO_3$ 0.8 g/L. The transformant culture was incubated at 30° C. with shaking at a constant speed of 200 rpm. From the start of fermentation (Day 0), 1 ml fermentation culture was taken on Days 2, 3, 4, and 6, centrifuged at 12000×g, and the supernatant was collected.

The supernatant of the transformant was measured for β-glucosidase activity. Enzyme activity assay: The β-glucosidase activity was determined according to the procedure as described by Venturi, et al. (Extracellular β-D-glucosidase from *Chaetomium thermophilum* var. *coprophilum*: production, purification and some biochemical properties, *J. Basic Microbiol.* 2002(42): 55-66).

One unit of enzyme activity of the glucosidase is defined as the amount of enzyme that produces 1.0 µM p-nitrophenol per minute from the substrate of 4 mM p-nitrophenyl-β-D-glucopyranoside in 100 mM sodium citrate with 0.01% TWEEN® 20 under the conditions of 50° C. and pH 5.

Figure 4:
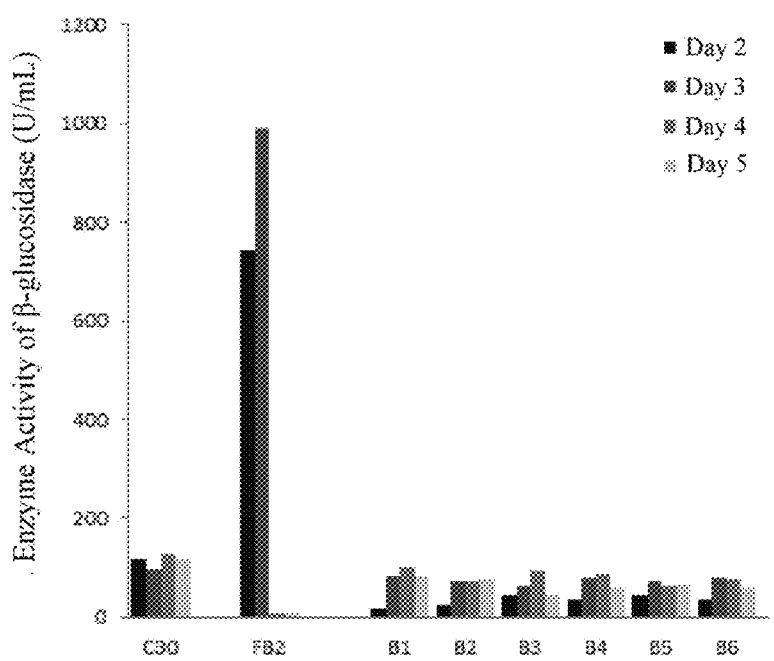
FIG. 4: Assay of the enzyme activity of β-glucosidase from Trichoderma reesei transformed with pAZ189 (B1, B2, B3, B4, B5, B6) and Trichoderma reesei transformed with pAZ193 (FB2). In the figure, C30 represents T. reesei RUT-C30.

The results show that, the enzyme activity of the β-glucosidase from all the transformants is comparable to that of *Trichoderma reesei* Rut-C30 throughout the fermentation. FIG. 4 exemplarily illustrates the enzyme activity of the transformants B1 to B6, and the enzyme activities of the remaining transformants are similar as those of the transformants B1 to B6 (results not shown).

Example 10

Screening of *Trichoderma reesei* Transformants of pAZ193 and Detection of Enzyme Activity The primary screening of the transformants obtained in Example 7 was carried out on screening plates for hygromycin resistance. The particular method makes reference to de Groot, M. J. et al., *Agrobacterium tumefaciens*-mediated transformation of filamentous fungi. *Nature Biotechnology*, 1998(16): 839-842.

After the primary screening, the spores were collected from the transformants for the fermentation for the enzyme production (referring to Chinese Patent Application CN200980107269 ("Over-expression of catalase in *Trichoderma*") for the fermentation conditions for the *T. reesei* transformants). The spore-plates of nine transformants were taken randomly, and washed with 3 ml 0.01% TWEEN® 80. In particular, several transformants were picked after primary screening; each transformant was individually inoculated onto hygromycin-resistant selection medium, and cultured at 30° C. for 5-7 days. Then, the plates were washed with 0.8% normal saline and the spores were collected into the suspension. The spores were inoculated into 50 ml cellulase-inducing medium in 250 ml glass shake flasks. The composition of the medium is as follows:

$(NH4)_2SO_4$ 5 g/L; MES buffer 19.52 g/L; yeast extract (OXOID, Cat. No. LP0021) 9 g/L; $KH_2PO_4$ 4.5 g/L; $CaCl_2 \cdot 2H_2O$ 1.32 g/L; $MgSO_4 \cdot 7H_2O$ 1 g/L; defoamer (purchased from Nanjing Huaxing Defoamers Co.; Cat. No. xp-m-130) 5 ml/L; 400× trace elements 2.5 ml/L pH 5.5; lactose (sterilized separately) 40 g/L, wherein, the solutions of 400× trace elements are: citric acid (anhydrous) 175 g/L; $FeSO_4 \cdot 7H_2O$ 200 g/L; $ZnSO_4 \cdot 7H_2O$ 16 g/L; $CuSO_4 \cdot 5H_2O$ 3.2 g/L; $MnSO_4 \cdot 4H_2O$ 1.4 g/L; $H_3BO_3$ 0.8 g/L.

The transformant culture was incubated at 30° C. with shaking at a constant speed of 200 rpm. From the day next to the start of fermentation, 1 ml fermentation culture was taken on Days 2, 3, 4, and 6, centrifuged at 12000×g, and the supernatant was collected.

The culture of the transformant was measured for β-glucosidase activity. The results show that, the pAZ193 *Trichoderma reesei* BGL1 transformant produces enzymes earlier and the enzyme activity is enhanced, wherein the enzyme activity of the transformant FB2 is significantly enhanced. FIG. 4 exemplarily shows the enzyme activity of the transformant numbered FB2, wherein the β-glucosidase activity of the FB2 transformant reaches ten times that of *T. reesei* Rut-C30 at Day 2 and Day 3, and is significantly higher than pAZ189 *T. reesei* BGL1 transformant. For example, for B1 to B6 in FIG. 4: PB2: 989.5 U/ml; pAZ189 *T. reesei* BGL1 transformant: 31.2-79.6 U/ML; *T. reesei* Rut-C30 97.21 U/ml; the above are the enzyme activity of Day 3. The enzyme activity of the other pAZ193 transformants also achieved the effects similar to FB2 (result not shown).

Example 11

Screening of *Trichoderma reesei* Transformants of pAZ301 and Detection of Enzyme Activity The transformation yielded about 300 transformants in total. After the primary screening, the spores were collected from the transformants for the fermentation for the enzyme production (referring to Chinese Patent Application CN200980107269 ("Over-expression of catalase in *Trichoderma*") for the fermentation conditions for the *T. reesei* transformants). The spore-plates of nine transformants were taken randomly, and washed with 3 ml 0.01% TWEEN® 80. In particular, several transformants were picked after primary screening; each transformant was individually inoculated onto hygromycin-resistant selection medium, and cultured at 30° C. for 5-7 days. Then, the plates were washed with 0.8% normal saline and the spores were collected into the suspension. The spores were inoculated into 50 ml cellulase-inducing medium in 250 ml glass shake flask. The composition of the medium is as follows:

$(NH4)_2SO_4$ 5 g/L; MES buffer 19.52 g/L; yeast extract (OXOID, Cat. No. LP0021) 9 g/L; $KH_2PO_4$ 4.5 g/L; $CaCl_2 \cdot 2H_2O$ 1.32 g/L; $MgSO_4 \cdot 7H_2O$ 1 g/L; defoamer (purchased from Nanjing Huaxing Defoamers Co., Cat. No. xp-m-130) 5 ml/L; 400× trace elements 2.5 ml/L pH 5.5; lactose (sterilized separately) 40 g/L, wherein, the solutions of 400× trace elements are: citric acid (anhydrous) 175 g/L; $FeSO_4 \cdot 7H_2O$ 200 g/L; $ZnSO_4 \cdot 7H_2O$ 16 g/L; $CuSO_4 \cdot 5H_2O$ 3.2 g/L; $MnSO_4 \cdot 4H_2O$ 1.4 g/L; $H_3BO_3$ 0.8 g/l.

The transformant culture was incubated at 30° C. with shaking at a constant speed of 200 rpm. 1 ml fermentation culture was taken on Days 2 and 3 of the fermentation, centrifuged at 12000×g, and their supernatant were collected.

Figure 5:
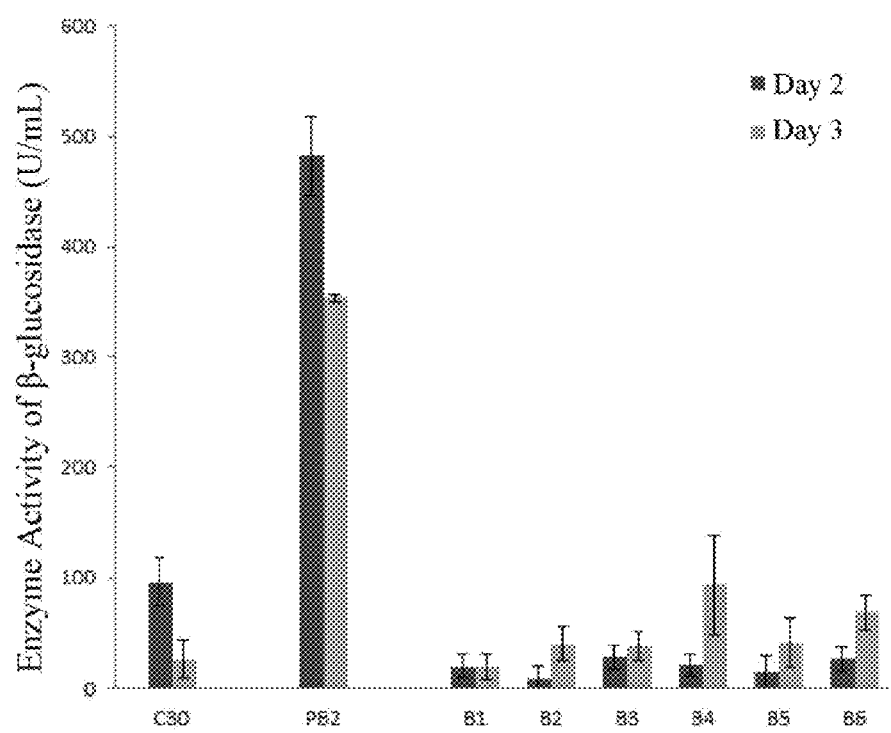
FIG. 5: Assay of the enzyme activity of β-glucosidase from Trichoderma reesei transformed with pAZ189 (B1, B2, B3, B4, B5, and B6) and Trichoderma reesei transformed with pAZ301 (PB2). In the figure, C30 represents T. reesei RUT-C30.

The culture of the transformant was measured for β-glucosidase activity. The results show that, the pAZ193 BGL1 *T. reesei* transformant produces enzymes earlier and the enzyme activity is enhanced, wherein the β-glucosidase activity of the transformant numbered PB2 reaches five times that of *T. reesei* Rut-C30 at Day 2 and Day 3, and is significantly higher than pAZ189 *T. reesei* BGL1 transformant. See FIG. 5: PB2: 482 U/ML; pAZ189 *T. reesei* BGL1 transformant: 8.3-28.4 U/ML; *T. reesei* Rut-C30 96.35 U/ml; the above data are the enzyme activity of Day 2. The other pAZ301 transformants also achieve the similar effects as PB2 (result not shown).

It is seen from the above Examples that, for the transformant obtained by transforming *T. reesei* RUT-C30 with BGL1 expression vector with aspartic protease (such as F1 or p6281) as a fusion fragment, its β-glucosidase activity reaches several times as high as that of *T. reesei* Rut-C30 on Day 2 or 3 of the fermentation, and is significantly higher than pAZ189 *T. reesei* BGL1 transformant. It demonstrates that the transformant having β-glucosidase fused to aspartic proteases (such as F1 or P6281) exhibits enzyme activity which is several times higher than that of the transformant without fusion fragment, and the time for achieving the peak enzyme production is shortened from 6-7 days to 2-3 days in terms of fermentation period.

All documents referred to in the present invention are incorporated herein by reference as if each document is individually incorporated as a reference. Further, it should also understood that, after reading the above teachings of the present invention, those skilled in the art can make various changes or modifications, and these equivalent forms again fall within the scope as defined by the appended claims.

The invention claimed is:

1. An isolated polynucleotide, wherein the polynucleotide encodes a fusion protein comprising sequentially from N-terminus to C-terminus:

(a) an aspartic protease of SEQ. ID NO: 3 or 7;
(b) a β-glucosidase of SEQ ID NO: 5; and
(c) optionally a linker sequence located between (a) and (b), which is encoded by the sequence as set forth in SEQ ID NO: 4.

2. The polynucleotide according to claim 1, wherein:
the aspartic protease is derived from a cellulose-degrading microorganism selected from Trichoderma, Penicil-

*lium, Aspergillus, Mucor, Botrytis, Cellulomonas, Cellvibrio, Cytophaga, Bacteroides succinogenes, Ruminococcus flavefaciens, R. albus*, and/or *Butyrivibrio fibrisolvens*.

3. The polynucleotide according to claim 1, wherein:
the β-glucosidase is derived from a cellulose-degrading microorganism, selected from *Trichoderma, Penicillium, Aspergillus, Mucor, Botrytis, Cellulomonas, Cellvibrio, Cytophaga, Bacteroides succinogenes, Ruminococcus flavefaciens, R. albus*, and/or *Butyrivibrio fibrisolvens*.

4. A recombinant expression vector comprising an isolated polynucleotide, wherein the polynucleotide encodes a fusion protein comprising sequentially from N-terminus to C-terminus:
 (a) an aspartic protease of SEQ ID NO: 3 or 7;
 (b) a β-glucosidase of SEQ ID NO: 5; and
 (c) optionally a linker sequence located between (a) and (b), which is encoded by the sequence as set forth in SEQ ID NO: 4.

5. The recombinant expression vector according to claim 4, wherein:
the aspartic protease is derived from a cellulose-degrading microorganism selected from *Trichoderma, Penicillium, Aspergillus, Mucor, Botrytis, Cellulomonas, Cellvibrio, Cytophaga, Bacteroides succinogenes, Ruminococcus flavefaciens, R. albus*, and/or *Butyrivibrio fibrisolvens*.

6. The recombinant expression vector according to claim 4, wherein:
the β-glucosidase is derived from a cellulose-degrading microorganism, selected from *Trichoderma, Penicillium, Aspergillus, Mucor, Botrytis, Cellulomonas, Cellvibrio, Cytophaga, Bacteroides succinogenes, Ruminococcus flavefaciens, R. albus*, and/or *Butyrivibrio fibrisolvens*.

7. The recombinant expression vector according to claim 4, characterized in that the recombinant expression vector further comprises one or more elements selected from the group consisting of:
 (i) a promoter;
 (ii) a signal peptide coding sequence;
 (iii) a leader peptide coding sequence;
 (iv) a terminator;
 (v) a marker gene; and
 (vi) a polyadenylation sequence.

8. The recombinant expression vector according to claim 4, characterized in that the basic skeleton of the recombinant expression vector is derived from: plasmid pCAmbia1300, plasmid pCAmbia2300, plasmid pCAmbia1301 or plasmid pBIN19.

9. A recombinant host cell comprising the polynucleotide according to claim 1.

10. The recombinant host cell of claim 9, wherein the host cell is *E. coli*, yeast or *Agrobacteriunm*.

11. The recombinant host cell of claim 9, wherein the host cell is derived from *Trichoderma, Aspergillus* or *Penicillium*.

12. The polynucleotide according to claim 1, wherein:
the aspartic protease is derived from *T. harzianum* or *T.reesei*, and/or the β-glucosidase is derived from *T. harzianum, T. reesei*, or *A. niger*.

13. The recombinant expression vector according to claim 4, wherein:
the aspartic protease is derived from *T. harzianum* or *T. reesei*, and/or the β-glucosidase is derived from *T. harzianum, T. reesei*, or *A. niger*.

14. The recombinant expression vector according to claim 4, characterized in that the recombinant expression vector is pAZ193.

15. The recombinant host cell of claim 9, wherein the host cell is *Saccharomyces cerevisiae, Pichia, Agrobacterium tumefaciens* or *Agrobacterium rhizogenes*.

16. The recombinant host cell of claim 9, wherein the host cell is derived from *T. harzianum, T. reesei*, or *A. niger*.

\* \* \* \* \*